(12) United States Patent
Kobelt

(10) Patent No.: US 8,827,188 B2
(45) Date of Patent: Sep. 9, 2014

(54) APPARATUS AND METHOD FOR DISTRIBUTING FLUID

(76) Inventor: Jacob Kobelt, Surrey (CA)

( * ) Notice: Subject to any disclaimer, the term of this patent is extended or adjusted under 35 U.S.C. 154(b) by 0 days.

(21) Appl. No.: 13/574,866

(22) PCT Filed: Jan. 25, 2010

(86) PCT No.: PCT/CA2010/000119
§ 371 (c)(1),
(2), (4) Date: Jul. 24, 2012

(87) PCT Pub. No.: WO2011/088544
PCT Pub. Date: Jul. 28, 2011

(65) Prior Publication Data
US 2012/0305591 A1    Dec. 6, 2012

(51) Int. Cl.
| | |
|---|---|
| *B05B 1/30* | (2006.01) |
| *A62C 31/02* | (2006.01) |
| *B05B 3/02* | (2006.01) |
| *B05B 15/06* | (2006.01) |
| *B05B 1/16* | (2006.01) |
| *A61M 3/00* | (2006.01) |
| *B05B 1/18* | (2006.01) |

(52) U.S. Cl.
CPC .............. *B05B 1/18* (2013.01); *B05B 1/1609* (2013.01); *A61M 3/005* (2013.01); *B05B 15/065* (2013.01)
USPC ............ 239/579; 239/569; 239/396; 239/438; 239/442; 239/443

(58) Field of Classification Search
CPC .......... B05B 1/30; B05B 3/02; B05B 1/3013; B05B 1/3033; B05B 1/3026; B05B 1/304; B05B 15/06; B05B 15/066; B05B 15/067; B05B 15/068; A62C 31/02; A62C 31/00; F23D 11/04
USPC ............ 239/579, 569, 396, 391, 397, 214.15, 239/436, 438, 440, 441, 442, 443, 444, 447, 239/448, 449
See application file for complete search history.

(56) References Cited

U.S. PATENT DOCUMENTS 3,624,073 A * 11/1971 Field et al. .................. 540/569
3,770,200 A    11/1973 Bauer et al.
(Continued)

FOREIGN PATENT DOCUMENTS

DE    4421424 A1    12/1995
DE    19609816 A1    9/1997
(Continued)

OTHER PUBLICATIONS

International Search Report mailed on Oct. 20, 2010 for PCT Patent Application No. PCT/CA2010/000119, 2 pages.
(Continued)

*Primary Examiner* — Justin Jonaitis
(74) *Attorney, Agent, or Firm* — Kilpatrick Townsend & Stockton LLP

(57) ABSTRACT

Methods and apparatuses for distributing fluid are disclosed. Fluid is received in an opening of a body, and at least some of the fluid is distributed to a first conduit in communication with a first outlet of a first discharge element coupled to said body. At least some of the fluid received in the opening is selectively distributed to a second conduit in communication with a second outlet of a second discharge element couplable to at least one of the body and the first discharge element in response to coupling and decoupling of the second discharge element.

41 Claims, 14 Drawing Sheets

(56) References Cited

U.S. PATENT DOCUMENTS

| | | | |
|---|---|---|---|
| 3,921,635 A | 11/1975 | Gauthier | |
| 4,330,089 A * | 5/1982 | Finkbeiner | 239/381 |
| 4,850,965 A | 7/1989 | Zinopoulos et al. | |
| 4,852,428 A * | 8/1989 | Haga et al. | 74/826 |
| 5,093,943 A | 3/1992 | Wei | |
| 5,146,639 A | 9/1992 | Krause | |
| 5,241,714 A | 9/1993 | Barry | |
| 6,190,365 B1 | 2/2001 | Abbott et al. | |
| 6,206,862 B1 | 3/2001 | Giamanco et al. | |
| 2005/0107752 A1 | 5/2005 | Su et al. | |
| 2007/0200009 A1 * | 8/2007 | Mueller | 239/444 |

FOREIGN PATENT DOCUMENTS

| | | |
|---|---|---|
| EA | 009854 B1 | 4/2008 |
| FR | 2872439 A3 | 1/2006 |
| JP | 61-181555 A | 8/1986 |
| JP | 3-96837 H | 10/1991 |
| JP | 2009-261743 A | 11/2009 |
| RU | 2126300 C1 | 2/1999 |
| RU | 2142342 C1 | 12/1999 |
| WO | 01/08538 A1 | 2/2001 |
| WO | 2007/007955 A1 | 1/2007 |
| WO | 2009/102402 A1 | 8/2009 |

OTHER PUBLICATIONS

Written Opinion of the International Searching Authority mailed on Oct. 20, 2010 for PCT Patent Application No. PCT/CA2010/000119, 4 pages.

First Office Action issued Sep. 3, 2013, for Japanese Patent Application No. 2012-550273, and English Translation, 4 pgs.

* cited by examiner

APPARATUS AND METHOD FOR DISTRIBUTING FLUID

This application is a U.S. National Phase under 35 USC 371 of PCT Application No. PCT/CA2010/000119 filed Jan. 25, 2010, the disclosure of which is incorporated by reference herein.

BACKGROUND OF THE INVENTION

1. Field of Invention

This invention relates generally to distributing fluid, and more particularly to methods and apparatuses for distributing fluid.

2. Description of Related Art

An apparatus for distributing fluid, such as a showerhead, for example, may receive fluid and distribute the fluid out a fluid dispensing end for various purposes such as bodily cleansing, for example. However, some known apparatuses for bodily cleansing have only a fixed-size fluid dispensing end, and thus are not easily adaptable to particular cleaning functions such as cleaning internal orifices, for example. Although other known fluid dispensing apparatuses do include selectable fluid dispensing ends of different sizes, these known apparatuses do not provide a simple mechanism for offering these selectable fluid dispensing ends of different sizes. Still other known fluid dispensing apparatuses provide only a single rate of fluid flow that is not automatically variable with the selected size of fluid dispensing end. These apparatuses may therefore disadvantageously offer too little fluid flow for general bodily cleansing, or an unduly high rate of flow for cleansing internal orifices, for example.

SUMMARY OF THE INVENTION

In accordance with one aspect of the invention, there is provided a method of distributing fluid. The method involves receiving the fluid in an opening of a body, distributing at least some fluid received in the opening to a first conduit in communication with a first outlet of a first discharge element coupled to the body, and selectively distributing at least some fluid received in the opening to a second conduit in communication with a second outlet of a second discharge element coupled to at least one of the body and the first discharge element. Selectively distributing the at least some fluid received in the opening to the second conduit involves controlling flow of fluid through a third conduit in communication with the opening and in communication with the second conduit when the second discharge element is coupled to the at least one of the body and the first discharge element. The flow of fluid through the third conduit is controlled in response to coupling and decoupling of the second discharge element with the at least one of the body and the first discharge element such that fluid is permitted to pass through the third conduit when the second discharge element is coupled to the at least one of the body and the first discharge element, and such that fluid is prevented from passing through the third conduit when the second discharge element is uncoupled with the at least one of the body and the first discharge element. The method further involves distributing at least some of the fluid received in the first conduit to the second conduit when the second discharge element is coupled to the at least one of the body and the first discharge element.

Controlling flow of fluid through the third conduit may involve positioning a valve in an open position wherein a valve seat of the valve is spaced apart from the third conduit to permit fluid to pass through the third conduit when the second discharge element is coupled to the at least one of the body and the first discharge element, and positioning the valve in a closed position wherein the valve seat contacts a surface surrounding the third conduit to prevent fluid from passing through the third conduit when the second discharge element is uncoupled with the at least one of the body and the first discharge element.

Positioning the valve in the open position may involve transmitting a force from the second discharge element to the valve.

Transmitting the force from the second discharge element to the valve may involve transmitting the force from the second discharge element to a valve head of the valve adjacent the second discharge element when the second discharge element is coupled to the at least one of the body and the first discharge element.

Positioning the valve in the closed position may involve resiliently urging the valve seat against the surface surrounding the third conduit.

The method may further involve locking the second discharge element to the at least one of the body and the first discharge element when the second discharge element is coupled to the at least one of the body and the first discharge element.

The method may further involve connecting the body to a fluid source such that the opening receives the fluid from the fluid source.

In accordance with another aspect of the invention, there is provided an apparatus for distributing fluid. The apparatus includes: a body having an opening for receiving the fluid; a first discharge element coupled to the body, and having a first outlet and a first conduit in communication with the first outlet; means for distributing at least some fluid received in the opening to the first conduit; a second discharge element couplable and uncoupable with at least one of the body and the first discharge element, and having a second outlet and a second conduit in communication with the second outlet; and means for selectively controlling flow of at least some fluid received in the opening to the second conduit. The means for selectively controlling flow includes a third conduit in communication with the opening and in communication with the second conduit when the second discharge element is coupled to the at least one of the body and the first discharge element. The flow of fluid through the third conduit is controlled in response to coupling and decoupling of the second discharge element with the at least one of the body and the first discharge element such that fluid is communicated through the third conduit when the second discharge element is coupled to the at least one of the body and the first discharge element and such that fluid is prevented from passing through the third conduit when the second discharge element is uncoupled with the at least one of the body and the first discharge element. The apparatus further includes means for distributing at least some fluid received in the first conduit to the second conduit when the second discharge element is coupled to the at least one of the body and the first discharge element.

The means for selectively controlling may further include: a valve having a valve seat positionable in an open position wherein the valve seat is spaced apart from the third conduit to permit fluid to pass through the third conduit, and in a closed position wherein the valve seat contacts a surface surrounding the third conduit to prevent fluid from passing through the third conduit; means for positioning the valve in the open position when the second discharge element is coupled to the at least one of the body and the first discharge element; and means for positioning the valve in the closed position when the second discharge element is uncoupled with the at least one of the body and the first discharge element.

The means for positioning the valve in the open position may include means for transmitting a force from the second discharge element to the valve.

The valve may have a valve head adjacent the second discharge element when the second discharge element is coupled to the at least one of the body and the first discharge element, and the means for transmitting the force from the second discharge element to the valve may include means for transmitting the force from the second discharge element to the valve head of the valve.

The means for positioning the valve in the closed position may include means for resiliently urging the valve seat against the surface surrounding the third conduit and positioning the valve in the closed position when the second discharge element is uncoupled with the at least one of the body and the first discharge element.

The apparatus may further include means for locking the second discharge element to the at least one of the body and the first discharge element when the second discharge element is coupled to the at least one of the body and the first discharge element.

The apparatus may further include means for connecting the body to a fluid source such that the opening receives the fluid from the fluid source.

In accordance with another aspect of the invention, there is provided an apparatus for distributing fluid. The apparatus includes: a body having an opening for receiving the fluid; a first discharge element coupled to the body, and having a first outlet and a first conduit in communication with the first outlet; a fluid distributor operably configured to distribute at least some fluid received in the opening to the first conduit; and a second discharge element couplable and uncouplable with at least one of the body and the first discharge element, and having a second outlet and a second conduit in communication with the second outlet. The second discharge element is operably configured to receive at least some fluid received in the first conduit when the second discharge element is coupled to the at least one of the body and the first discharge element. The apparatus further includes a flow controller that selectively controls flow of at least some fluid received in the opening to the second conduit, the flow controller defining a third conduit in communication with the opening and in communication with the second discharge element when the second discharge element is coupled to the at least one of the body and the first discharge element. The flow controller includes a valve cooperating with the third conduit and being controlled in response to coupling and decoupling of the second discharge element with the at least one of the body and the first discharge element such that fluid is communicated through the third conduit when the second discharge element is coupled to the at least one of the body and the first discharge element and such that fluid is prevented from passing through the third conduit when the second discharge element is uncoupled with the at least one of the body and the first discharge element.

The valve may have a valve seat, and the valve may be positionable in an open position wherein the valve seat is spaced apart from the third conduit to permit fluid to pass through the third conduit, and in a closed position wherein the valve seat contacts a surface of the flow controller surrounding the third conduit to prevent fluid from passing through the third conduit.

The second discharge element may be operably configured to transmit a force to the valve and position the valve in the open position when the second discharge element is coupled to the at least one of the body and the first discharge element.

The valve may have a valve head adjacent the second discharge element when the second discharge element is coupled to the at least one of the body and the first discharge element, and the second discharge element may be operably configured to transmit the force to the valve head of the valve.

The apparatus may further include a resilient device operably configured to resiliently urge the valve in the closed position, and to position the valve in the closed position when the second discharge element is uncoupled with the at least one of the body and the first discharge element.

The resilient device may be operably configured to contact the valve seat of the valve to resiliently urge the valve in the closed position.

The resilient device may include a spring.

The spring may include a coned-disc spring.

The apparatus may further include a lock operably configured to lock the second discharge element to the at least one of the body and the first discharge element when the second discharge element is coupled to the at least one of the body and the first discharge element.

The apparatus may further include a connector operably configured to connect the body to a fluid source such that the opening receives the fluid from the fluid source.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings that illustrate embodiments of the invention.

DETAILED DESCRIPTION

Figure 1:
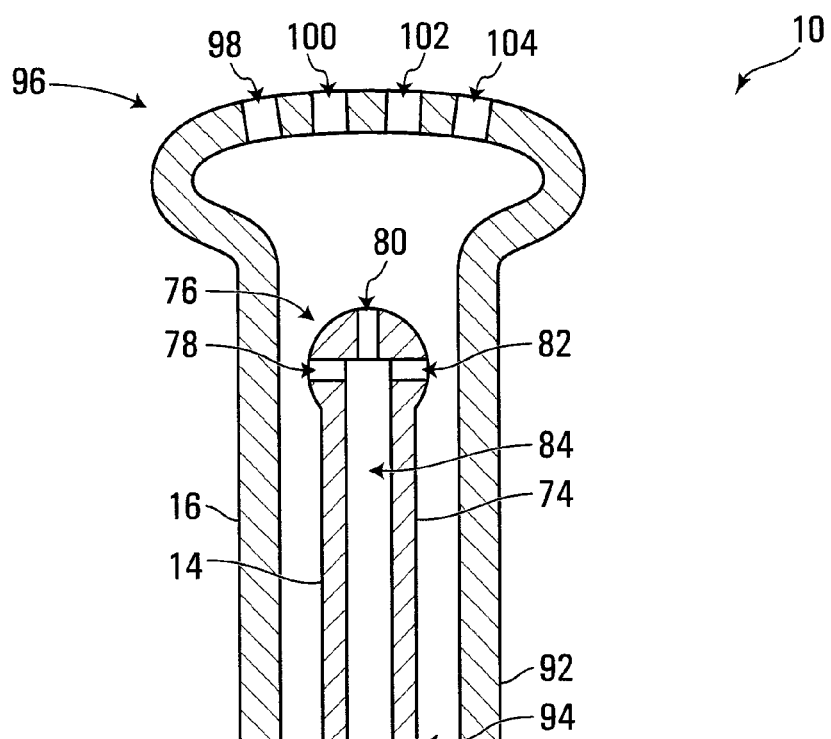
FIG. 1 is a cross-sectional view of an apparatus for dispensing fluid in accordance with a first embodiment of the invention.
Figure 1:
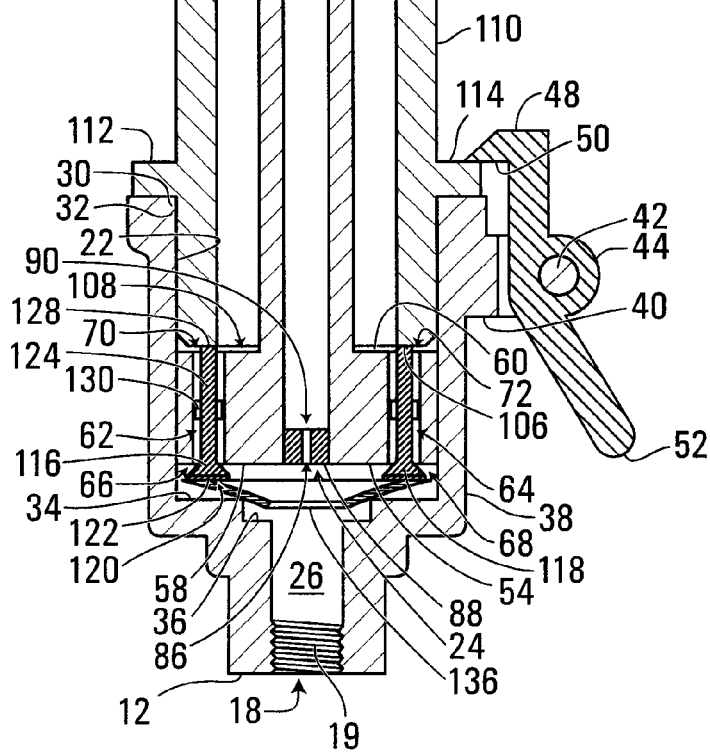

Referring to FIG. 1, an apparatus for distributing fluid, in accordance with a first embodiment of the invention, is shown generally at 10. The apparatus 10 includes a body 12, a first discharge element 14, and a second discharge element 16.

Figure 2:
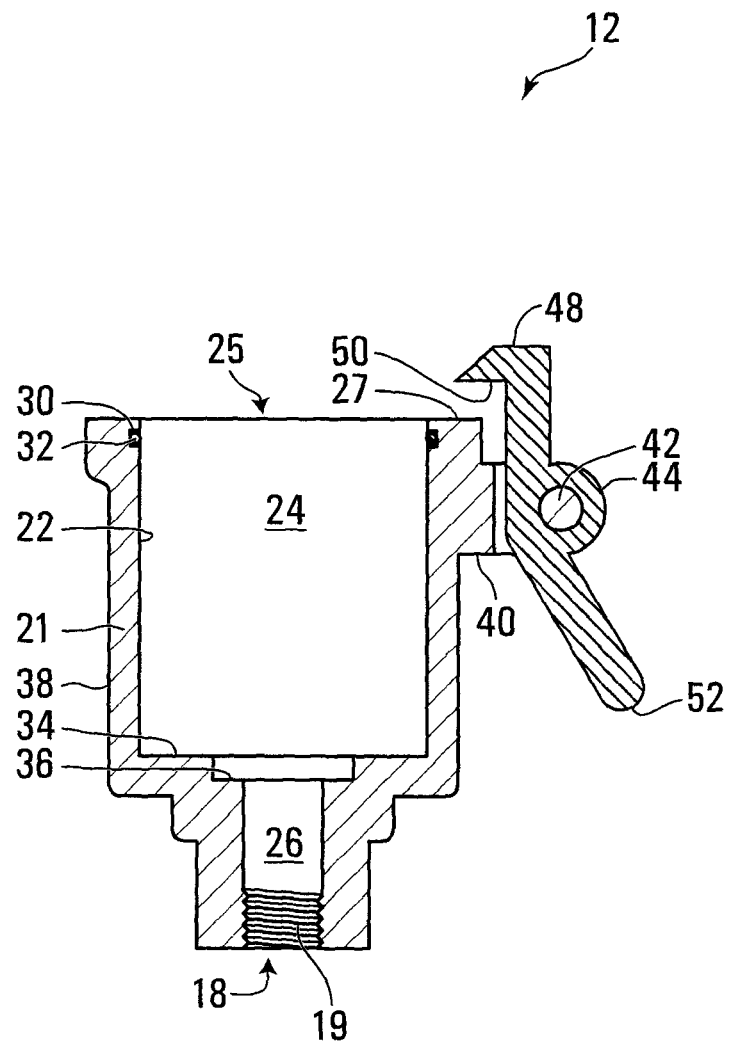
FIG. 2 is a cross-sectional view of a body of the apparatus of FIG. 1.

Referring to FIG. 2, the body 12 has an opening 18 for receiving a fluid. In the embodiment shown, the body 12 defines internal threads 19 proximate the opening 18, and the internal threads 19 may cooperate with external threads of a fluid source (not shown) such as a showerhead hose, for example. The internal threads 19 thus function as a connector to connect the body 12 to the fluid source such that the opening 18 receives fluid from the fluid source.

The body 12 in the embodiment shown has an annular wall 21 having an inner surface 22 that defines a generally cylindrical cavity 24 having an opening 25. The wall 21 has an annular rim 27 surrounding the opening 25. A conduit 26 is formed in the body 12 and is in communication with the opening 18 and the cavity 24. Adjacent the opening 25, the inner surface 22 also defines an annular groove 30 that holds an o-ring 32. The inner surface 22 also has an end portion 34 that defines an annular recess 36 in communication with the conduit 26.

The wall 21 also has an outer surface 38 and a generally radial projection 40. The projection 40 includes a pivot 42 for pivotally holding a lock, which in the embodiment shown is a lock lever 44. On one side of the pivot 42, the lock lever 44 has a holding portion 48 having a holding surface 50 facing the rim 27 and spaced apart therefrom for locking the second discharge element 16 (shown in FIG. 1) to the body 12. On an opposite side of the pivot 42, the lock lever 44 also has an actuator portion 52 for receiving a force to rotate the lock lever 44 about the pivot 42, thereby moving the holding surface 50 away from the second discharge element 16 to facilitate coupling and uncoupling the second discharge element 16 with the body 12.

Figure 3:
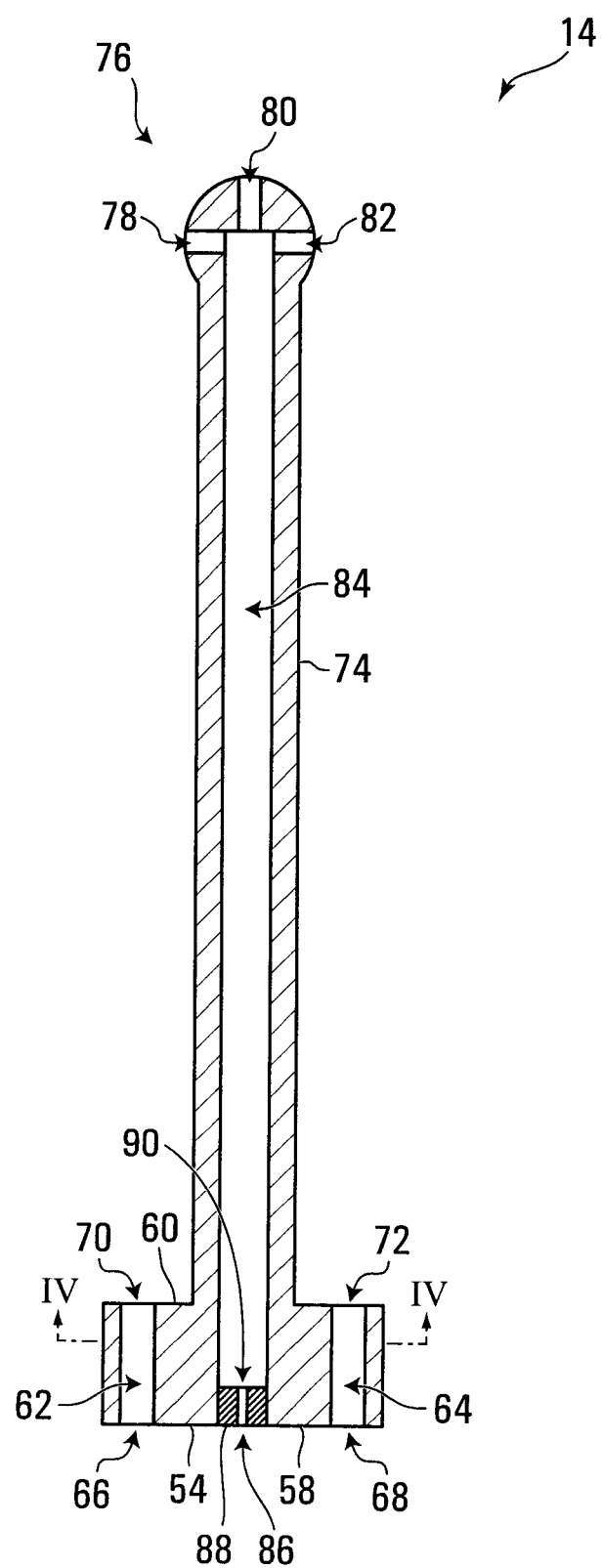
FIG. 3 is a first cross-sectional view of a first discharge element of the apparatus of FIG. 1.
Figure 4:
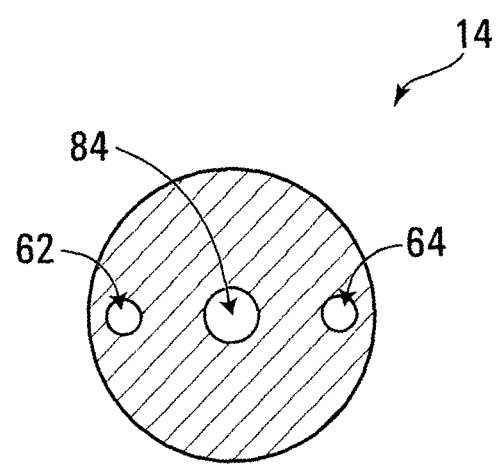
FIG. 4 is a second cross-sectional view of the first discharge element of FIG. 3, shown along the line IV-IV shown in FIG. 3.

Referring to FIGS. 3 and 4, the first discharge element 14 includes a generally cylindrical base 54. The base 54 has a generally circular end surface 58 and an opposed generally annular surface 60. The base 54 also defines first and second axial and diametrically opposed conduits 62 and 64. The first and second conduits 62 and 64 extend between respective openings 66 and 68 in the end surface 58 and respective openings 70 and 72 in the annular surface 60.

The first discharge element 14 also includes an elongate projection 74 extending axially from the base 54. The projection 74 has a fluid dispensing end shown generally at 76 having openings that define outlets 78, 80, and 82. Although three outlets 78, 80, and 82 are shown, the fluid dispensing end 76 may, in alternative embodiments, include one or more outlets. The projection 74 also defines a conduit 84 in communication with an opening 86 in the end surface 58 and with the outlets 78, 80, and 82. The first discharge element 14 also includes a fluid flow limiter 88 held by an adhesive in the conduit 84 proximate the opening 86. The fluid flow limiter 88 defines an orifice 90 for permitting fluid flow through the conduit 84 at a limited rate.

Figure 5:
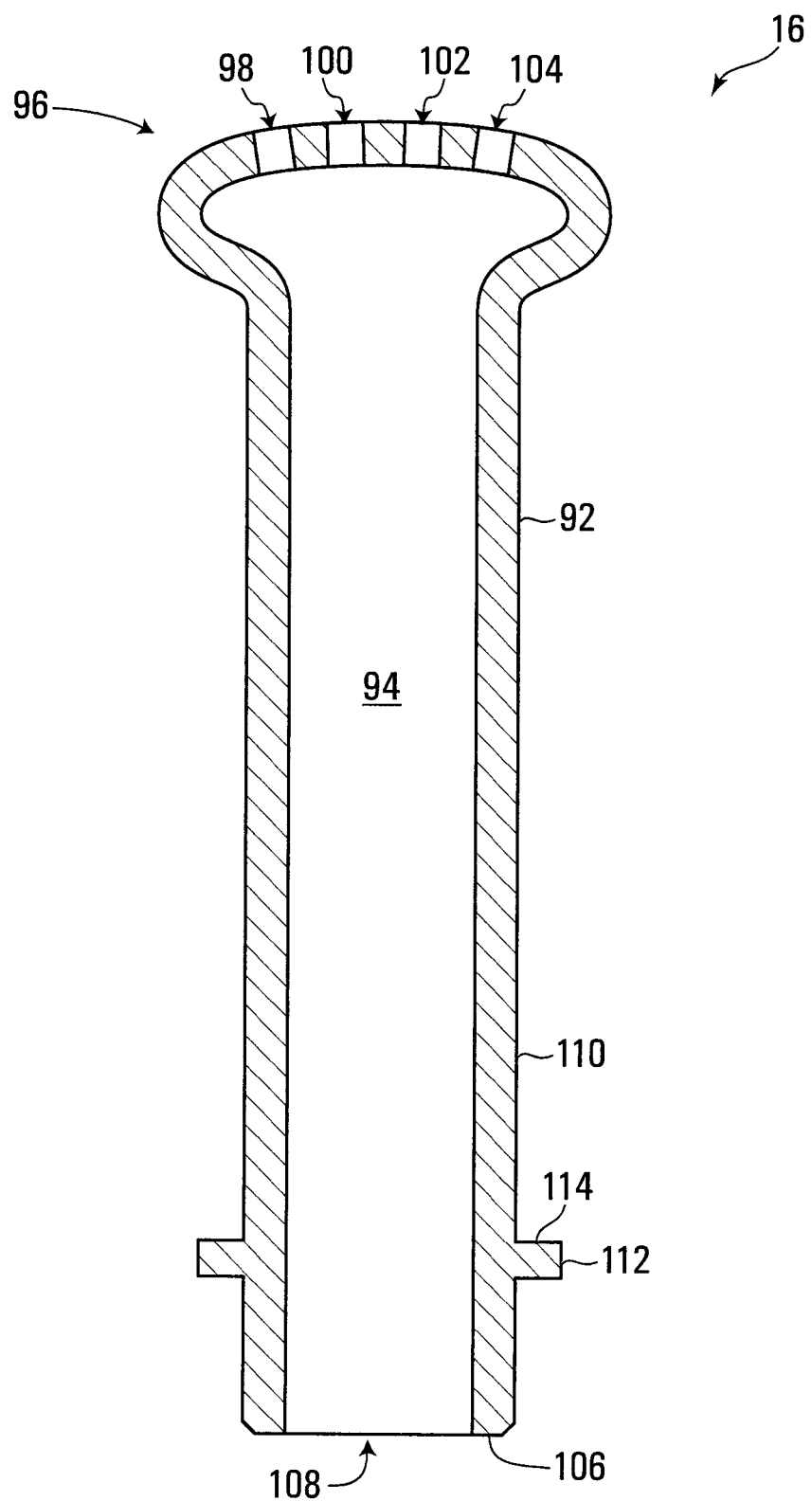
FIG. 5 is a cross-sectional view of a second discharge element of the apparatus of FIG. 1.

Referring to FIG. 5, the second discharge element 16 includes an elongate projection 92 defining a conduit 94 therethrough. The projection 92 has a fluid dispensing end shown generally at 96, which has openings defining outlets 98, 100, 102, and 104. Although four outlets 98, 100, 102, and 104 are shown, it will be appreciated that in alternative embodiments, the fluid dispensing end 96 may include one or more outlets. The second discharge element 16 is shown unitarily formed, although the fluid dispensing end 96 may alternatively be detachable from the remainder of the projection 92. The projection 92 has an annular end wall 106 defining an opening 108, and the conduit 94 is in communication with the opening 108 and with the outlets 98, 100, 102, and 104. The projection 92 has an outer wall 110 defining an annular flange 112 having a holding surface 114 for cooperating with the holding surface 50 (shown in FIG. 2) to lock the second discharge element 16 to the body 12 (shown in FIGS. 1 and 2).

Figure 6:
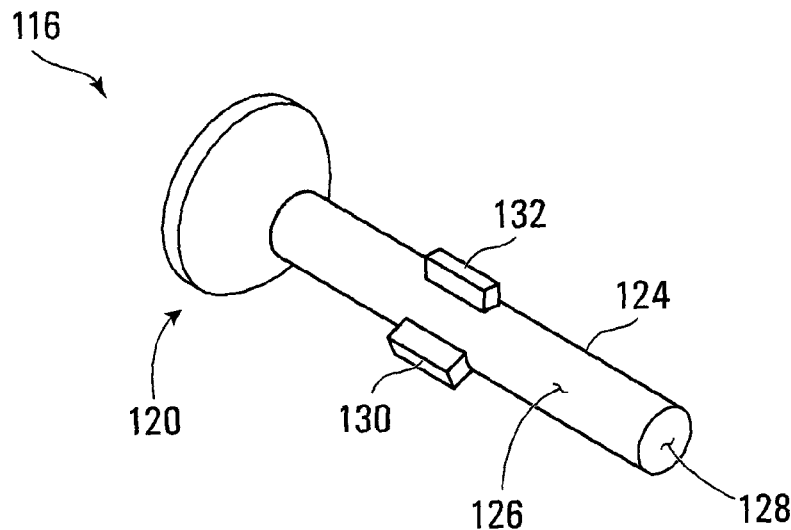
FIG. 6 is a first perspective view of a first valve of the apparatus of FIG. 1.
Figure 7:
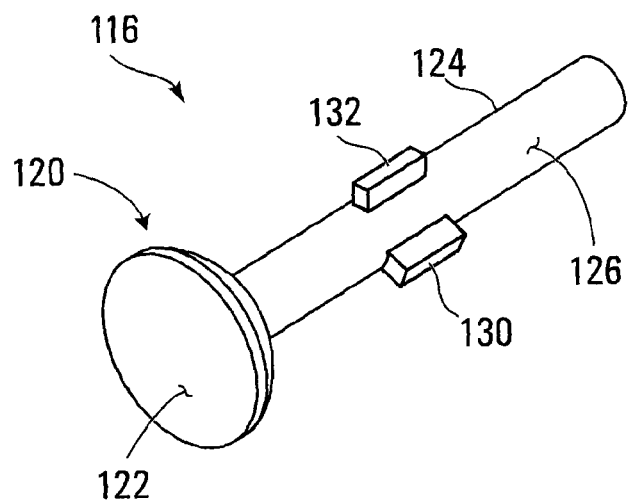
FIG. 7 is a second perspective view of the valve of FIG. 6.
Figure 8:
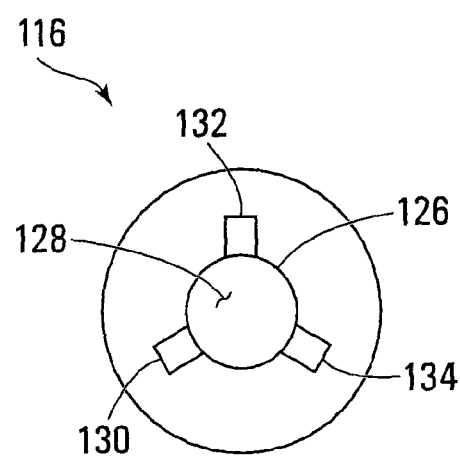
FIG. 8 is a plan view of the valve of FIG. 6.

Referring back to FIG. 1, the apparatus 10 includes first and second valves 116 and 118 in the first and second conduits 62 and 64 respectively. Referring to FIGS. 6, 7, and 8, the first valve 116 includes a generally tapered valve seat 120 having a circular end surface 122, and a valve stem 124 extending axially from the valve seat 120 opposite the end surface 122. The valve stem 124 has a cylindrical outer wall 126 and a valve head 128. The outer wall 126 defines generally radial projections 130, 132, and 134. The second valve 118 is generally the same as the first valve 116.

Referring back to FIG. 1, in the embodiment shown, the apparatus 10 includes a coned-disc spring 136 positioned against the end portion 34 of the inner surface 22 of the body 12 and extending into the annular recess 36. The valve stem 124 of the first valve 116 is received within the first conduit 62 such that the valve seat 120 contacts a surface of the base 54 surrounding the opening 66 in the end surface 58 of the first discharge element 14, and the valve head 128 protrudes out the opening 70 in the annular surface 60. The projections 130, 132, and 134 (also shown in FIGS. 6, 7, and 8) slidably contact an inner wall of the first conduit 62 to center the valve stem 124 of the first valve 116 axially in the first conduit 62. The second valve 118 is similarly received within the second conduit 64.

The first discharge element 14 is coupled to the body 12 by fixing, with an adhesive for example, a portion of the internal surface 22 of the body 12 with an outer surface of the base 54 of the first discharge element 14. In this manner, the end surface 122 of the first valve 116 contacts the spring 136, as does a corresponding surface of the second valve 118. Also, the openings 66, 68, and 86 in the end surface 58 of the first discharge element 14 are received within the cavity 24 of the body 12 in communication with the conduit 26 and the opening 18, and the first and second conduits 62 and 64 are thus in fluid communication with the cavity 24, the conduit 26, and the opening 18.

As shown in FIG. 1, the second discharge element 16 is coupled to the body 12 by receiving a portion of the projection 92 of the second discharge element 16 in the cavity 24 of the body 12. The annular flange 112 contacts the body 12, and the holding surface 114 of the second discharge element 16 contacts the holding surface 50 of the lock lever 44. The lock lever 44 thus locks the second discharge element 16 to the body 12 when the second discharge element 16 is coupled to the body 12. In alternative embodiments, other mechanisms, such as a twist lock, quick discharge or camlock, or horseshoe type retainer, for example, may lock the second discharge element 16 to the body 12 when the second discharge element 16 is coupled to the body 12.

As further shown in FIG. 1, when the second discharge element 16 is coupled to the body 12, the conduit 94 is in communication with the openings 70 and 72 of the annular surface 60 of the first discharge element 14, and the conduit 94 is thus in communication with the first and second conduits 62 and 64. Also, when the second discharge element 16 is coupled to the body 12, the conduit 94 is in communication with the outlets 78, 80, and 82 of the first discharge element 14, and the o-ring 32 contacts the outer wall 110 of the second discharge element 16 to seal the cavity 24. Therefore, when the second discharge element 16 is coupled to the body 12, at least some of the fluid received in the conduit 84 of the first discharge element 14 is distributed to the conduit 94 of the second discharge element 16, and the conduit 94 of the second discharge element 16 thus receives at least some fluid received in the conduit 84 of the first discharge element 14.

Also as shown in FIG. 1, when the second discharge element 16 is coupled to the body 12, the end wall 106 of the second discharge body contacts the valve head 128 of the first valve 116, and a corresponding surface of the second valve 118. The valve head 128 of the first valve 116, and a corresponding surface of the second valve 118, are thus adjacent the second discharge element 16 when the second discharge element 16 is coupled to the body 12. When the second discharge element 16 is coupled to the body 12, the second discharge element 16 transmits a force on the valve head 128 of the first valve 116, and on a corresponding surface of the second valve 118. This force causes the first and second valves 116 and 118 to be urged against the spring 136. The valve seat 120 of the first valve 116 is thus positioned away from the opening 66 of the first discharge element 14, and the first valve 116 is in an open position permitting fluid to flow from the opening 18 through the first conduit 62. Likewise, the second valve 118 is thus moved to an open position, permitting fluid to flow from the opening 18 through the second conduit 64. Therefore, the end wall 106 of the second discharge element 16 positions the first and second valves 116 and 118 in the respective open positions when the second discharge element 16 is coupled to the body 12.

The lock lever 44 may be urged, by a coil spring (not shown) for example, in a locked position whereby the holding surface 50 of the lock lever 44 contacts the holding surface 114 of the second discharge element 16 to lock the second discharge element 16 to the body 12 when the second discharge element 16 is coupled to the body 12. By actuating the actuator portion 52 of the lock lever 44, the holding surface 50 of the lock lever 44 is separated from the holding surface 114 of the second discharge element 16, and the second discharge element 16 may be removed from the cavity 24 of the body 12 and thus uncoupled from the body 12.

Figure 9:
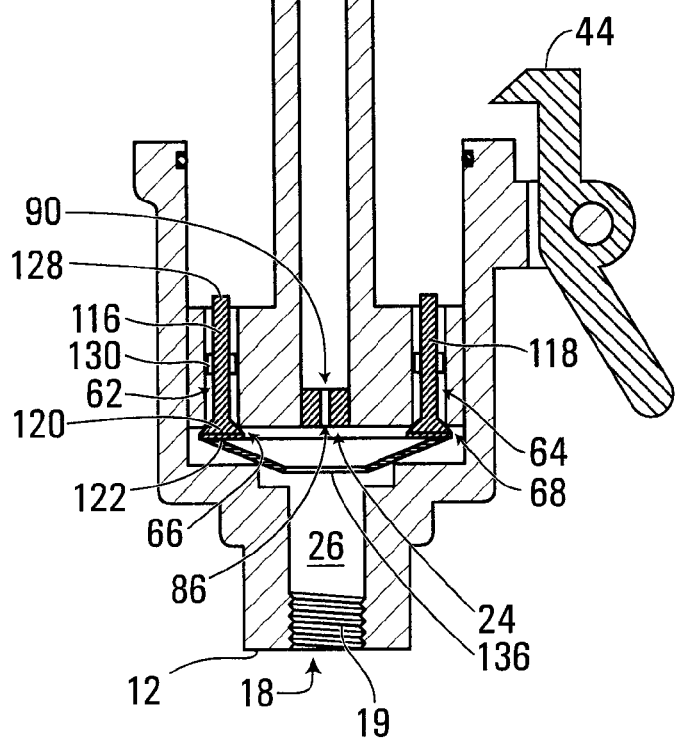
FIG. 9 is a cross-sectional view of the apparatus of FIG. 1, with the second discharge element of FIG. 5 uncoupled from the body of FIG. 2.

Referring to FIG. 9, the apparatus 10 is shown with the second discharge element 16 uncoupled from the body 12. When the second discharge element 16 is uncoupled from the body 12, the end wall 106 of the second discharge element no longer contacts the valve head 128 of the first valve 116 or a corresponding surface of the second valve 118. The spring 136 contacts the end surface 122 of the first valve 116, and a corresponding surface of the second valve 118. The spring 136 thus resiliently urges the end surface 122 of the valve seat 120 of the first valve 116 against a portion of the end surface 58 surrounding the opening 66 of the first discharge element 14, and resiliently urges a corresponding portion of the second valve 118 against the opening 68 of the first discharge element 14. The first and second valves 116 and 118 are thus resiliently urged in closed positions that close the openings 66 and 68, and thereby prevent fluid flowing through the first and second conduits 62 and 64 respectively, when the second discharge element 16 is uncoupled from the body 12. The spring 136 is therefore a resilient device that positions the first and second valves 116 and 118 in the respective closed positions when the second discharge element 16 is uncoupled from the body 12.

Referring back to FIG. 1, in operation, the body 12 is connected to a fluid source (not shown) such that the opening 18 receives fluid from the fluid source. When the second discharge element 16 is coupled to the body 12, the first and second valves 116 and 118 are positioned in the respective open positions. Fluid received through the opening 18 of the body 12 may therefore pass through the conduit 26, into the cavity 24, through the first and second conduits 62 and 64, and into the conduit 94 of the second discharge element 16. Simultaneously, when the second discharge element 16 is coupled to the body 12, fluid received through the opening 18 of the body 12 may pass through the conduit 26, into the cavity 24, through the orifice 90 of the fluid flow limiter 88, into the conduit 84 of the first discharge element 14, out the outlets 78, 80, and 82 of the first discharge element 14, and into the conduit 94 of the second discharge element 16. The fluid received in the conduit 94 of the second discharge element 16, which as described above may be received from the first conduit 62, the second conduit 64, or the conduit 84 of the first discharge element 14, exits the second discharge element 16 through the outlets 98, 100, 102, and 104. Therefore, some fluid received at the opening 18 is distributed to the conduit 84 of the first discharge element 14, and when the user couples the second discharge element 16 to the body 12, some other fluid received at the opening 18 is thereby selectively distributed to the conduit 94 of the second discharge element 16 through the first and second conduits 62 and 64. In some embodiments, the user may couple the second discharge element 16 to the body 12 for ordinary shower use, for example.

Alternatively, a user may actuate the actuator portion 52 and uncouple the second discharge element 16 from the body 12. When the second discharge element 16 is uncoupled from the body 12, the spring 136 positions the first and second valves 116 and 118 in the respective closed positions, and therefore fluid received through the opening 18 is prevented from passing through the first and second conduits 62 and 64. Fluid received through the opening 18 may therefore pass through the conduit 26, into the cavity 24, through the orifice 90 of the fluid flow limiter 88, through the conduit 84 of the first discharge element 14, and out the outlets 78, 80, and 82 thereof. However, when the second discharge element 16 is coupled to the body 12, additional fluid flows through the first and second conduits 62 and 64. Therefore, fluid is discharged from the apparatus 10 at a greater flow rate when the second discharge element 16 is coupled to the body 12, and at a reduced flow rate when the second discharge element 16 is uncoupled from the body 12.

The first and second valves 116 and 118 therefore cooperate with the first discharge element 14 to function as a flow controller that selectively distributes at least some fluid received in the opening 18 to the conduit 94 of the second discharge element 16 by selectively controlling flow of fluid through the first and second conduits 62 and 64 in response to coupling and decoupling of the second discharge element 16 with the body 12 such that fluid is permitted to pass through the first and second conduits 62 and 64 when the second discharge element 16 is coupled to the body 12, and fluid is prevented from passing through the first and second conduits 62 and 64 when the second discharge element 16 is uncoupled from the body 12. Regardless of whether the second discharge element 16 is coupled to the body 12, the body 12 and the first discharge element 14 act as a fluid distributor that distributes at least some fluid received at the opening 18 to the conduit 84 of the first discharge element 14.

The fluid dispensing end 76 of the first discharge element 14 is smaller than the fluid dispensing end 96 of the second discharge element 16, and therefore in the operational mode illustrated in FIG. 9, the user advantageously has a reduced fluid discharge area, and also at a reduced fluid volume as indicated above. The operational mode illustrated in FIG. 1 may be suitable for general cleansing, for example, and the operational mode illustrated in FIG. 9 may be suitable for particular applications, such as internal bodily cleansing also known as douching, for example. The apparatus 10 may therefore function as a showerhead for cleansing and hygiene, for example.

Figure 10:
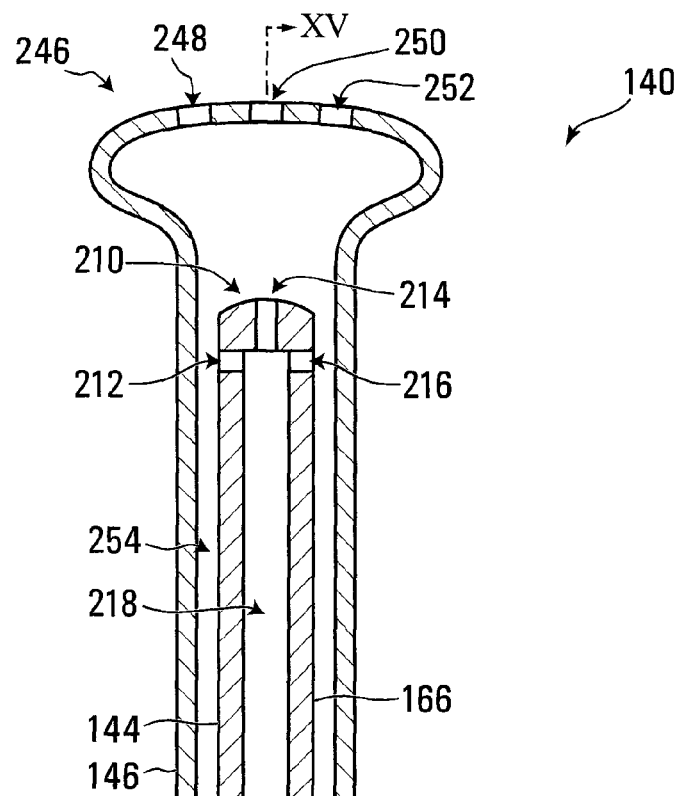
FIG. 10 is a first cross-sectional view of an apparatus for dispensing fluid in accordance with a second embodiment of the invention.

Referring to FIG. 10, an apparatus for distributing fluid, in accordance with a second embodiment of the invention, is shown generally at 140. The apparatus 140 includes a body 142, a first discharge element 144, and a second discharge element 146.

Figure 11:
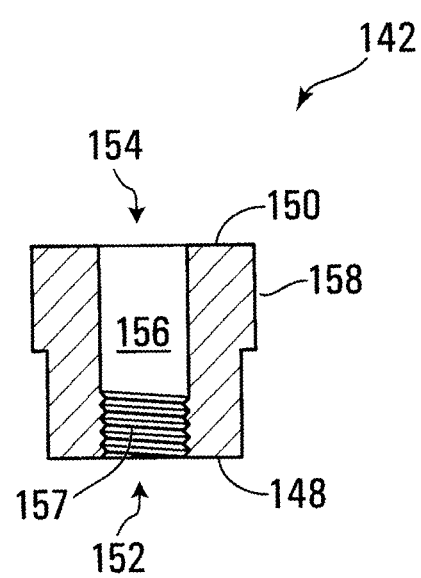
FIG. 11 is a cross-sectional view of a body of the apparatus of FIG. 10.

Referring to FIG. 11, the body 142 in the embodiment shown includes a generally annular wall having a first annular end surface 148 and a second annular end surface 150. The end surfaces 148 and 150 have respective openings 152 and 154, and the body 142 has a conduit 156 extending between the openings 152 and 154. The body 142 defines internal threads 157 proximate the opening 152. The internal threads 157 may cooperate with internal threads of a fluid source (not shown) such as a showerhead hose, for example, and the internal threads 157 thus function as a connector to connect the body 142 to the fluid source such that the opening 152 receives fluid from the fluid source.

Figure 12:
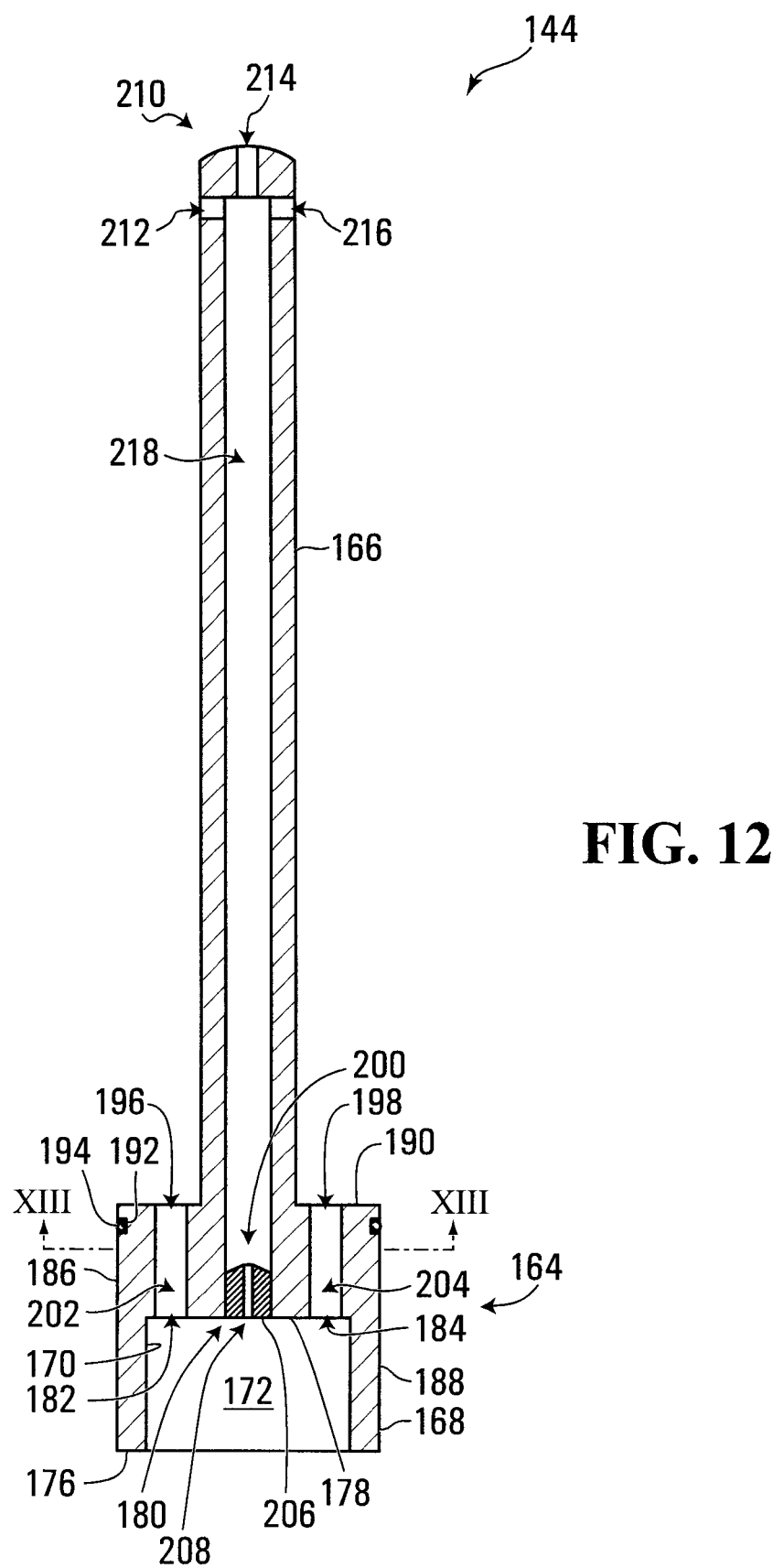
FIG. 12 is a first cross-sectional view of a first discharge element of the apparatus of FIG. 10.

Referring to FIG. 12, the first discharge element 144 includes a generally cylindrical base shown generally at 164 and a projection 166 projecting axially from the base 164. The base 164 includes an annular wall 168 having an inner surface 170 defining a cavity 172. The annular wall 168 also includes an annular end surface 176, and the base 164 has a circular end surface circular end surface 178 adjacent the cavity 172. The end surface 178 has a central opening 180 and diametrically opposed openings 182 and 184 in communication with the cavity 172.

The base 164 also has a generally cylindrical portion 186 having an outer surface 188 and a generally annular end surface 190. The outer surface 188 defines an annular groove 192 for holding an O-ring 194, and the end surface 190 has openings 196 and 198 axially aligned with the openings 182 and 184 respectively of the end surface 178.

Figure 13:
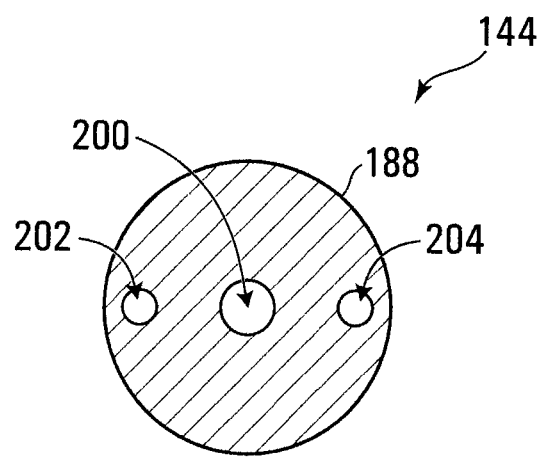
FIG. 13 is a second cross-sectional view of the first discharge apparatus of FIG. 12, shown along the line XIII-XIII shown in FIG. 12.

Referring to FIGS. 12 and 13, the generally cylindrical portion 186 of the base 164 defines a conduit 200 in communication with the opening 180 of the end surface 178, a conduit 202 in communication with the openings 182 and 196 of the end surfaces 178 and 190 respectively, and a conduit 204 in communication with the openings 184 and 198 of the end surfaces 178 and 190 respectively.

Referring back to FIG. 12, the first discharge element 144 also has a fluid flow limiter 206 in the conduit 200 proximate the opening 180. The fluid flow limiter 206 defines an orifice 208 for permitting fluid flow through the conduit 200 at a limited rate.

The projection 166 has a fluid dispensing end shown generally at 210 and having openings that define outlets 212, 214, and 216. Although three outlets 212, 214, and 216 are shown, the fluid dispensing end 210 may, in alternative embodiments, include one or more outlets. The projection 166 also defines a conduit 218 in communication with the conduit 200, the opening 180, and the outlets 212, 214, and 216.

Figure 14:
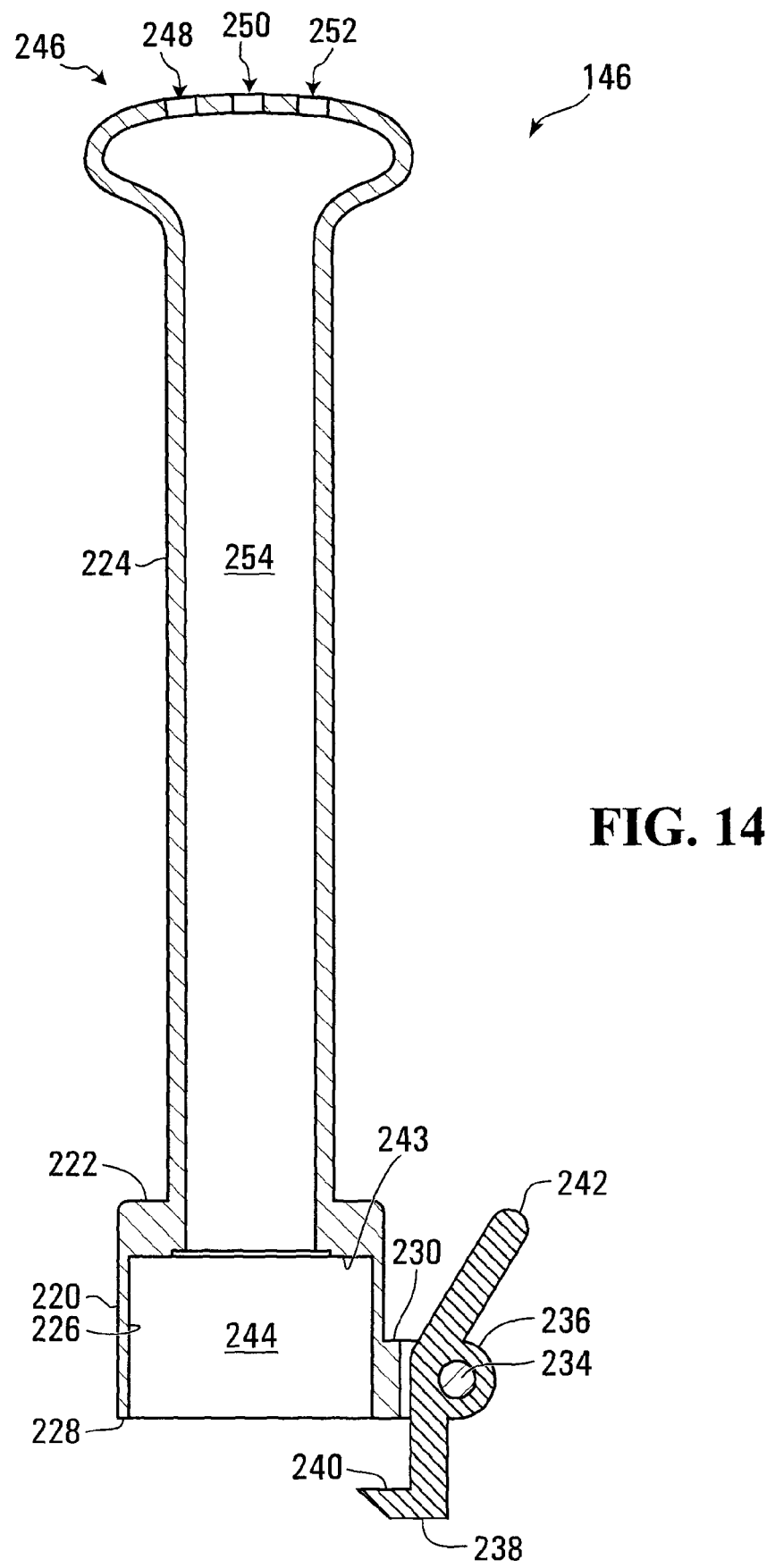
FIG. 14 is a cross-sectional view of a second discharge element of the apparatus of FIG. 10.

Referring to FIG. 14, the second discharge element 146 has a generally annular wall 220, a generally annular end wall 222 adjacent the wall 220, and an elongate projection 224 projecting axially away from the end wall 222 opposite the wall 220. The wall 220 has a cylindrical inner surface 226 and a generally annular rim 228. The wall 220 also has a generally radial projection 230 having a pivot 234 for pivotally holding a lock, which in the embodiment shown is a lock lever 236. On one side of the pivot 234, the lock lever 236 has a holding portion 238 having a holding surface 240 facing the rim 228 and spaced apart therefrom for locking the second discharge element 146 to the first discharge element 144 (shown in FIGS. 10, 12, and 13). On an opposite side of the pivot 234, the lock lever 236 also has an actuator portion 242 for receiving a force to rotate the lock lever 236 about the pivot 234, thereby moving the holding surface 240 away from the first discharge element 144 to facilitate coupling and uncoupling the second discharge element 146 with the first discharge element 144.

The end wall 222 has an inner surface 243, and the inner surfaces 226 and 243 define a generally cylindrical cavity 244.

The projection 224 has a fluid dispensing end shown generally at 246 and having openings that define outlets 248, 250, and 252. Although three outlets 248, 250, and 252 are shown, the fluid dispensing end 246 may, in alternative embodiments, include one or more outlets. The second discharge element 146 is shown unitarily formed, although the fluid dispensing end 246 may alternatively be detachable from the remainder of the projection 224. The projection 224 also defines a conduit 254 in communication with the cavity 244 and with the outlets 248, 250, and 252.

Figure 15:
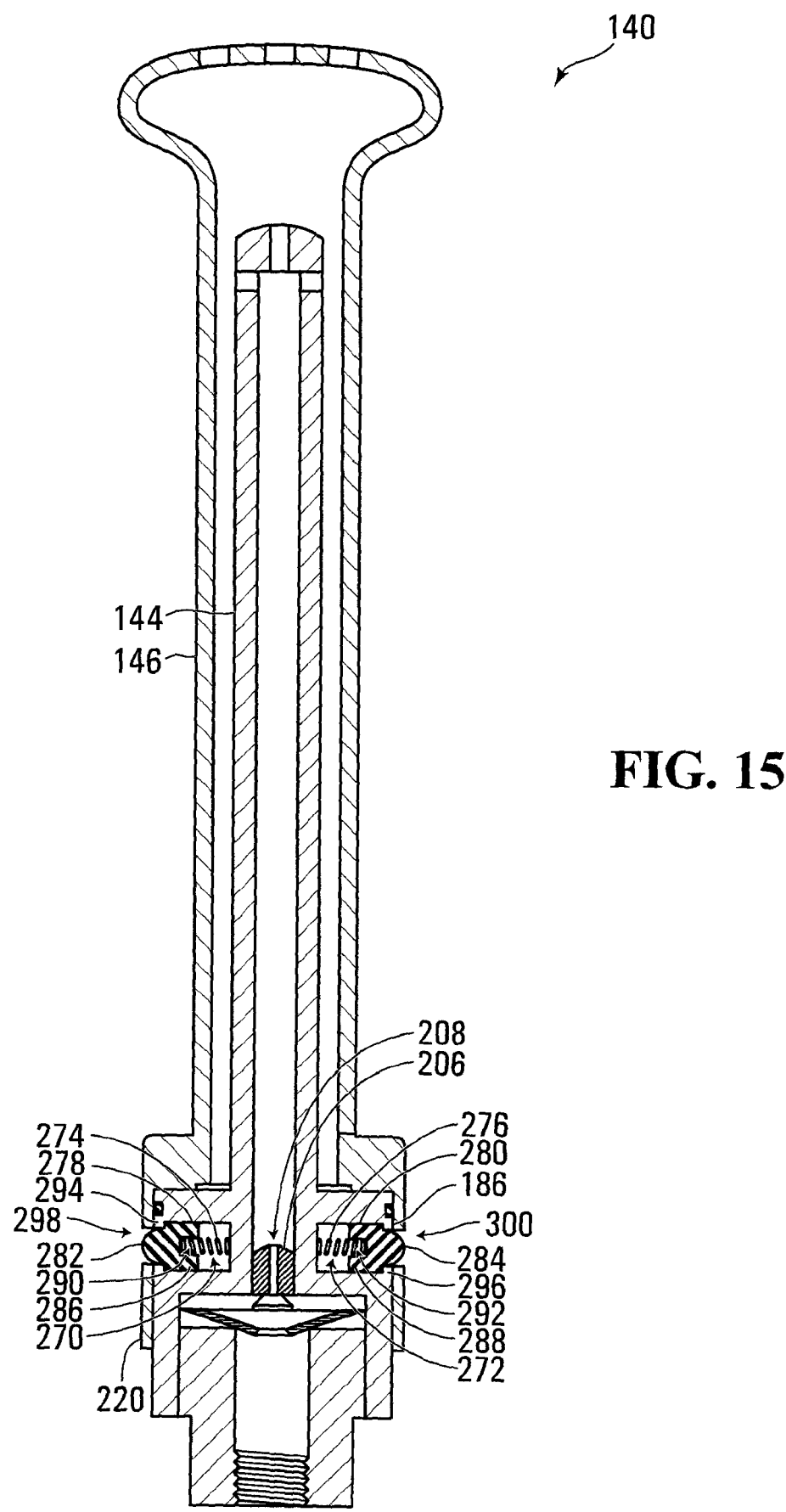
FIG. 15 is a second cross-sectional view of the apparatus of FIG. 10, shown along the line XV-XV shown in FIG. 10.

Referring to FIG. 15, the cylindrical portion 186 of the first discharge element 144 has opposed radially extending generally cylindrical cavities 270 and 272 holding respective coil springs 274 and 276 and respective locks, which in the embodiment shown are slidable bodies 278 and 280 having respective holding portions 282 and 284, and respective annular walls 286 and 288 defining respective receptacles 290 and 292 receiving the coil springs 274 and 276 respectively. The holding portions 282 and 284 have diameters less than the walls 286 and 288, and thus the walls 286 and 288 are held behind shoulders 294 and 296 respectively formed by the cylindrical portion 186, and the shoulders 294 and 296 thus hold the bodies 278 and 280 in the cavities 270 and 272 respectively. The wall 220 of the second discharge element 146 defines radially opposed openings 298 and 300 for receiving the holding portions 282 and 284 respectively. When the second discharge element 146 is coupled to the first discharge element 144 as shown in FIG. 10, the holding portions 282 and 284 are received in the openings 298 and 300 respectively, and thus cooperate with the lock lever 236 (shown in FIG. 10) to lock the second discharge element 146 to the first discharge element 144 when the second discharge element 146 is coupled to the first discharge element 144. Alternatively, one or more of the lock lever 236 and the bodies 278 and 280 may be omitted.

Referring back to FIG. 10, the apparatus 140 includes a first valve 256 in the conduit 202, and a second valve 258 in the conduit 204. The first and second valves 256 and 258 are substantially the same as the first valve 116 shown in FIGS. 6, 7, and 8. The first and second valves 256 and 258 therefore have valve seats 260 and 262 respectively that are substantially the same as the valve seat 120 shown in FIGS. 6, 7, and 8, and valve heads 264 and 266 that are substantially the same as the valve head 128 shown in FIGS. 6, 7, and 8. The first and second valves 256 and 258 are received in the conduits 202 and 204 respectively similarly to the first valve 116 in the conduit 62 (shown in FIG. 1). Therefore, the valve seats 260 and 262 of the first and second valves 256 and 258 respectively are adjacent the openings 182 and 184 respectively of the first discharge element 144. The apparatus 140 also includes a coned-disc spring 268 positioned against the end surface 150 of the body 142.

The first discharge element 144 is coupled to the body 142 by fixing, with an adhesive for example, a portion of the internal surface 170 of the first discharge element 144 with a portion of the outer surface 158 of the body 142. In this manner, the valve seats 260 and 262 of the first and second valves 256 and 258 respectively contact the spring 268. Also, the opening 154 of the body 142 is received within the cavity 172 of the first discharge element 144 and the conduits 202 and 204 are therefore in communication with the conduit 156 and opening 152 of the body 142.

As shown in FIG. 10, the second discharge element 146 is coupled to the first discharge element 144 by receiving the projection 166 of the first discharge element 144 in the conduit 254 of the second discharge element 146, and by receiving the cylindrical portion 186 of the first discharge element 144 in the cavity 244 (shown in FIG. 14) of the second discharge element 146. The O-ring 194 slidably contacts the inner surface 226 of the second discharge element 146, and the end surface 190 of the first discharge element 144 contacts the inner surface 243 of the second discharge element 146. Also, the holding surface 240 of the lock lever 236 contacts the end surface 176 of the first discharge element 144. The lock lever 236 thus locks the second discharge element 146 to the first discharge element 144 when the second discharge element 146 is coupled to the first discharge element 144. Referring to FIG. 15, the holding portions 282 and 284 are simultaneously received in the openings 298 and 300 respectively, and thus also lock the second discharge element 146 to the first discharge element 144 when the second discharge element 146 is coupled to the first discharge element 144. In alternative embodiments, other mechanisms, such as a twist lock, quick discharge or cam lock, or horseshoe type retainer, for example, may lock the second discharge element 146 to the first discharge element 144 when the second discharge element 146 is coupled to the first discharge element 144.

Referring back to FIG. 10, when the second discharge element 146 is coupled to the first discharge element 144, the conduit 254 of the second discharge element 146 is in communication with the openings 196 and 198, and thus the conduits 202 and 204, of the first discharge element 144. Also, as shown in FIG. 10, when the second discharge element 146 is coupled to the first discharge element 144, the conduit 254 of the second discharge element 146 is in communication with the outlets 212, 214, and 216 of the first discharge element 144, and therefore when the second discharge element 146 is coupled to the first discharge element 144, at least some of the fluid received in the conduit 218 of the first discharge element 144 is distributed to the conduit 254 of the second discharge element 146, and the conduit 254 of the second discharge element 146 thus receives at least some fluid received in the conduit 218 of the first discharge element 144.

Also as shown in FIG. 10, when the second discharge element 146 is coupled to the first discharge element 144, the inner surface 243 of the second discharge element 146 contacts the valve heads 264 and 266 of the first and second valves 256 and 258 respectively. The valve heads 264 and 266 are thus adjacent the second discharge element 146 when the second discharge element 146 is coupled to the first discharge element 144. When the second discharge element 146 is coupled to the first discharge element 144, the second discharge element 146 transmits a force on the valve heads 264 and 266. This force causes the first and second valves 256 and 258 to be urged against the spring 268. The valve seats 260 and 262 are thus positioned away from the openings 182 and 184 of the first discharge element 144 and the first and second valves 256 and 258 are thus moved to respective open positions permitting fluid to flow from the opening 152 through the conduits 202 and 204 respectively. Therefore, the inner surface 243 of the end wall 222 of the second discharge element 146 positions the first and second valves 256 and 258 in the respective open positions when the second discharge element 146 is coupled to the first discharge element 144.

Referring to FIGS. 10 and 15, the lock lever 236 may be urged, by a coil spring (not shown) for example, in a locked position whereby the holding surface 240 of the lock lever 236 contacts the end surface 176 of the first discharge element 144 to lock the second discharge element 146 to the first discharge element 144 when the second discharge element 146 is coupled to the first discharge element 144. By actuating the actuator portion 242 of the lock lever 236, the holding surface 240 of the lock lever 236 is separated from the end surface 176 of the first discharge element 144. Simultaneously, the holding portions 282 and 284 may be urged inwards and separated from the openings 298 and 300 of the second discharge element 146. When the holding surface 240 of the lock lever 236 is separated from the end surface 176, and the holding portions 282 and 284 are separated from the openings 298 and 300, the second discharge element 146 may be uncoupled from the first discharge element 144.

Figure 16:
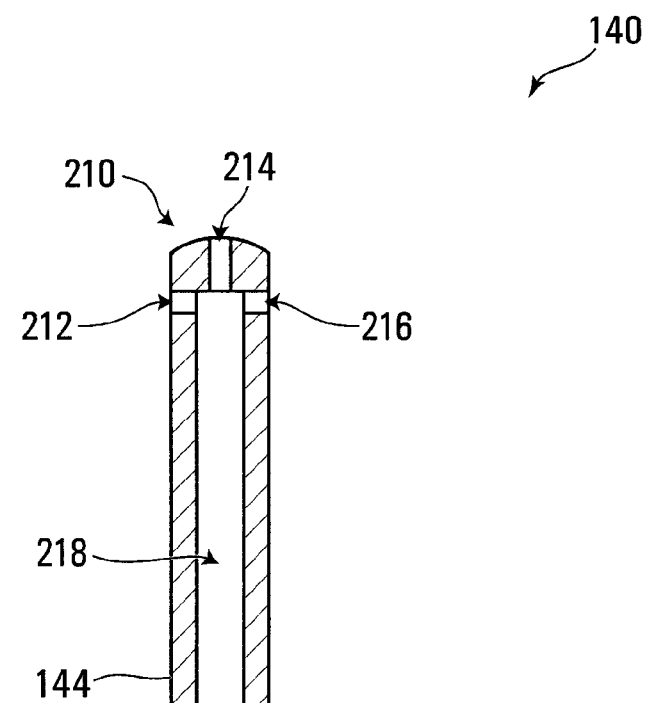
FIG. 16 is the cross-sectional view of the apparatus of FIG. 10, with the second discharge element of FIG. 14 uncoupled from the body of FIG. 11.

Referring to FIG. 16, the apparatus 140 is shown with the second discharge element 146 uncoupled from the first discharge element 144. When the second discharge element 146 is uncoupled from the first discharge element 144, the inner surface 243 of the second discharge element 146 (shown in FIG. 14) no longer contacts the valve heads 264 and 266 of the first and second valves 256 and 258 respectively. The spring 268 contacts the valve seats 260 and 262 of the first and second valves 256 and 258 respectively, and thus resiliently urges the valve seats 260 and 262 against respective surfaces portions of the first discharge element 144 surrounding the openings 182 and 184 respectively. The spring 268 thus resiliently urges the first and second valves 256 and 258 in closed positions that close the openings 182 and 184, thereby preventing fluid flowing through the conduits 202 and 204 respectively when the second discharge element 146 is uncoupled from the first discharge element 144. The spring 268 is therefore a resilient device that positions the first and second valves 256 and 258 in the respective closed positions when the second discharge element 146 is uncoupled from the first discharge element 144.

Referring back to FIG. 10, in operation, the body 142 is connected to a fluid source (not shown) such that the opening 152 receives fluid from the fluid source. When the second discharge element 146 is coupled to the first discharge element 144, the first and second valves 256 and 258 are positioned in the respective open positions. Fluid received through the opening 152 of the body 142 may therefore pass through the conduit 156, into the cavity 172, through the conduits 202 and 204, and into the conduit 254 of the second discharge element 146. Simultaneously, when the second discharge element 146 is coupled to the first discharge element 144, fluid received in the opening 152 of the body 142 may pass through the conduit 156, into the cavity 172, through the orifice 208 of the fluid flow limiter 206 into the conduits 200 and 218 of the first discharge element 144, out the outlets 212, 214, and 216 of the first discharge element 144, and into the conduit 254 of the second discharge element 146. The fluid received in the conduit 254 of the second discharge element 146, which as described above may be received from the conduit 202, the conduit 204, or the conduits 200 and 218 of the first discharge element 144, exits the second discharge element 146 through the outlets 248, 250, and 252. Therefore, some fluid received at the opening 152 is distributed to the conduits 208 and 218 of the first discharge element 144, and when the user couples the second discharge element 146 to the first discharge element 144, some other fluid received at the opening 152 is thereby selectively distributed to the conduit 254 of the second discharge element 146. In some embodiments, the user may couple the second discharge element 146 to the first discharge element 144 for ordinary shower use, for example.

Alternatively, a user may actuate the actuator portion 242 and the holding portions 282 and 284 (shown in FIG. 15) to uncouple the second discharge element 146 from the first discharge element 144. When the second discharge element 146 is uncoupled from the first discharge element 144, the spring 268 positions the first and second valves 256 and 258 in the respective closed positions, and therefore fluid received through the opening 152 is prevented from passing through the conduits 202 and 204. Fluid received through the opening 152 may therefore pass through the conduit 156, into the cavity 172, through the orifice 208 of the fluid flow limiter 206 through the conduits 200 and 218 of the first discharge element 144, and out the outlets 212, 214, and 216 thereof. However, when the second discharge element 146 is coupled to the first discharge element 144, additional fluid flows through the conduits 202 and 204 and fluid is discharged from the apparatus 140 at a greater flow rate when compared to when the second discharge element 146 is uncoupled from the first discharge element 144.

The first and second valves 256 and 258 therefore cooperate with the first discharge element 144 to function as a flow controller that selectively distributes at least some fluid received in the opening 152 to the conduit 254 of the second discharge element 146 by selectively controlling flow of fluid through the conduits 202 and 204 in response to coupling and decoupling of the second discharge element 146 with the first discharge element 144 such that fluid is permitted to pass through the conduits 202 and 204 when the second discharge element 146 is coupled to the first discharge element 144, and fluid is prevented from passing through the conduits 202 and 204 when the second discharge element 146 is uncoupled from the first discharge element 144. Regardless of whether the second discharge element 146 is coupled to the first discharge element 144, the body 142 and the first discharge element 144 act as a fluid distributor that distributes at least some fluid received at the opening 152 to the conduits 200 and 218 of the first discharge element 144.

As in the apparatus 10 shown in FIG. 1, the fluid dispensing end 210 of the first discharge element 144 is smaller than the fluid dispensing end 246 of the second discharge element 146, and therefore in the operational mode illustrated in FIG. 16, the user advantageously has reduced fluid discharge area and a reduced fluid volume. The operational mode illustrated in FIG. 10 may be suitable for general cleansing, for example, and the operational mode illustrated in FIG. 16 may be suitable for particular applications, such as internal bodily cleansing also known as douching, for example. The apparatus 140 may therefore function as a showerhead for cleansing and hygiene, for example.

While specific embodiments of the invention have been described and illustrated, such embodiments should be considered illustrative of the invention only and not as limiting the invention as construed in accordance with the accompanying claims.

What is claimed is:

1. A method of distributing fluid, the method comprising:
    receiving the fluid in an opening of a body;
    distributing at least some fluid received in said opening to a first conduit in communication with a first outlet of a first discharge element coupled to said body;
    selectively distributing at least some fluid received in said opening, other than said fluid distributed to said first conduit, to a second conduit in communication with a second outlet of a second discharge element coupled to at least one of said body and said first discharge element;
    wherein selectively distributing said at least some fluid received in said opening to said second conduit comprises controlling flow of fluid through a third conduit in communication with said opening and in communication with said second conduit when said second discharge element is coupled to said at least one of said body and said first discharge element, said flow of fluid through said third conduit being controlled in response to coupling and decoupling of said second discharge element with said at least one of said body and said first discharge element such that fluid is permitted to pass through said third conduit when said second discharge element is coupled to said at least one of said body and said first discharge element and such that fluid is prevented from passing through said third conduit when said second discharge element is uncoupled with said at least one of said body and said first discharge element; and
    distributing at least some of said fluid received in said first conduit to said second conduit when said second discharge element is coupled to said at least one of said body and said first discharge element.

2. The method of claim 1 wherein controlling flow of fluid through said third conduit comprises:
    positioning a valve in an open position wherein a valve seat of said valve is spaced apart from said third conduit to permit fluid to pass through said third conduit when said second discharge element is coupled to said at least one of said body and said first discharge element; and
    positioning said valve in a closed position wherein said valve seat contacts a surface surrounding said third conduit to prevent fluid from passing through said third conduit when said second discharge element is uncoupled with said at least one of said body and said first discharge element.

3. The method of claim 2 wherein positioning said valve in said open position comprises transmitting a force from said second discharge element to said valve.

4. The method of claim 3 wherein transmitting said force from said second discharge element to said valve comprises transmitting said force from said second discharge element to a valve head of said valve adjacent said second discharge element when said second discharge element is coupled to said at least one of said body and said first discharge element.

5. The method of claim 2 wherein positioning said valve in said closed position comprises resiliently urging said valve seat against said surface surrounding said third conduit.

6. The method of claim 1 further comprising locking said second discharge element to said at least one of said body and said first discharge element when said second discharge element is coupled to said at least one of said body and said first discharge element.

7. The method of claim 1 further comprising connecting said body to a fluid source such that said opening receives the fluid from said fluid source.

8. The method of claim 1 wherein said second discharge element defines a plurality of outlets comprising said second outlet.

9. The method of claim 1 wherein said second outlet is the only outlet of said second discharge element.

10. The method of claim 1 wherein said second discharge element comprises a fluid dispensing end unitarily formed with said second discharge element.

11. The method of claim 1 wherein said second discharge element is attachable to and detachable from a fluid dispensing end.

12. The method of claim 1 wherein distributing said at least some of said fluid received in said first conduit to said second conduit comprises distributing said at least some of said fluid received in said first conduit to said second conduit through said first outlet.

13. An apparatus for distributing fluid, the apparatus comprising:
a body having an opening for receiving the fluid;
a first discharge element coupled to said body, and having a first outlet and a first conduit in communication with said first outlet;
means for distributing at least some fluid received in said opening to said first conduit;
a second discharge element couplable and uncouplable with at least one of said body and said first discharge element, and having a second outlet and a second conduit in communication with said second outlet;
means for selectively controlling flow of at least some fluid received in said opening, other than said fluid distributed to said first conduit, to said second conduit, said means for selectively controlling flow comprising a third conduit in communication with said opening and in communication with said second conduit when said second discharge element is coupled to said at least one of said body and said first discharge element, said flow of fluid through said third conduit being controlled in response to coupling and decoupling of said second discharge element with said at least one of said body and said first discharge element such that fluid is communicated through said third conduit when said second discharge element is coupled to said at least one of said body and said first discharge element and such that fluid is prevented from passing through said third conduit when said second discharge element is uncoupled with said at least one of said body and said first discharge element; and
means for distributing at least some fluid received in said first conduit to said second conduit when said second discharge element is coupled to said at least one of said body and said first discharge element.

14. The apparatus of claim 13 wherein said means for selectively controlling further comprises:
a valve having a valve seat positionable in an open position wherein said valve seat is spaced apart from said third conduit to permit fluid to pass through said third conduit, and in a closed position wherein said valve seat contacts a surface surrounding said third conduit to prevent fluid from passing through said third conduit;
means for positioning said valve in said open position when said second discharge element is coupled to said at least one of said body and said first discharge element; and
means for positioning said valve in said closed position when said second discharge element is uncoupled with said at least one of said body and said first discharge element.

15. The apparatus of claim 14 wherein said means for positioning said valve in said open position comprises means for transmitting a force from said second discharge element to said valve.

16. The apparatus of claim 15 wherein:
said valve has a valve head adjacent said second discharge element when said second discharge element is coupled to said at least one of said body and said first discharge element; and
said means for transmitting said force from said second discharge element to said valve comprises means for transmitting said force from said second discharge element to said valve head of said valve.

17. The apparatus of claim 14, wherein said means for positioning said valve in said closed position comprises means for resiliently urging said valve seat against said surface surrounding said third conduit and positioning said valve in said closed position when said second discharge element is uncoupled with said at least one of said body and said first discharge element.

18. The apparatus of claim 13 further comprising means for locking said second discharge element to said at least one of said body and said first discharge element when said second discharge element is coupled to said at least one of said body and said first discharge element.

19. The apparatus of claim 13 further comprising means for connecting said body to a fluid source such that said opening receives the fluid from said fluid source.

20. The apparatus of claim 13 wherein said second discharge element defines a plurality of outlets comprising said second outlet.

21. The apparatus of claim 13 wherein said second outlet is the only outlet of said second discharge element.

22. The apparatus of claim 13 wherein said second discharge element comprises a fluid dispensing end unitarily formed with said second discharge element.

23. The apparatus of claim 13 wherein said second discharge element is attachable to and detachable from a fluid dispensing end.

24. The apparatus of claim 13 wherein the apparatus is a showerhead.

25. The apparatus of claim 13 wherein said means for distributing said at least some fluid received in said first conduit to said second conduit comprises means for distributing said at least some of said fluid received in said first conduit to said second conduit through said first outlet.

26. An apparatus for distributing fluid, the apparatus comprising:
a body having an opening for receiving the fluid;
a first discharge element coupled to said body, and having a first outlet and a first conduit in communication with said first outlet;
a fluid distributor operably configured to distribute at least some fluid received in said opening to said first conduit;
a second discharge element couplable and uncouplable with at least one of said body and said first discharge element, and having a second outlet and a second conduit in communication with said second outlet, wherein said second discharge element is operably configured to receive at least some fluid received in said first conduit when said second discharge element is coupled to said at least one of said body and said first discharge element; and
a flow controller that selectively controls flow of at least some fluid received in said opening, other than said fluid distributed to said first conduit, to said second conduit, said flow controller defining a third conduit in communication with said opening and in communication with said second discharge element when said second discharge element is coupled to said at least one of said body and said first discharge element, said flow controller comprising a valve cooperating with said third conduit and being controlled in response to coupling and decoupling of said second discharge element with said at least one of said body and said first discharge element such that fluid is communicated through said third conduit when said second discharge element is coupled to said at least one of said body and said first discharge element and such that fluid is prevented from passing through said third conduit when said second discharge element is uncoupled with said at least one of said body and said first discharge element.

27. The apparatus of claim 26 wherein:
said valve has a valve seat; and
said valve is positionable in an open position wherein said valve seat is spaced apart from said third conduit to permit fluid to pass through said third conduit, and in a closed position wherein said valve seat contacts a surface of said flow controller surrounding said third conduit to prevent fluid from passing through said third conduit.

28. The apparatus of claim 27 wherein said second discharge element is operably configured to transmit a force to said valve and position said valve in said open position when said second discharge element is coupled to said at least one of said body and said first discharge element.

29. The apparatus of claim 28 wherein said valve has a valve head adjacent said second discharge element when said second discharge element is coupled to said at least one of said body and said first discharge element, and wherein said second discharge element is operably configured to transmit said force to said valve head of said valve.

30. The apparatus of claim 27 further comprising a resilient device operably configured to resiliently urge said valve in said closed position, and to position said valve in said closed position when said second discharge element is uncoupled with said at least one of said body and said first discharge element.

31. The apparatus of claim 30 wherein said resilient device is operably configured to contact said valve seat of said valve to resiliently urge said valve in said closed position.

32. The apparatus of claim 30 wherein said resilient device comprises a spring.

33. The apparatus of claim 32 wherein said spring comprises a coned-disc spring.

34. The apparatus of claim 26 further comprising a lock operably configured to lock said second discharge element to said at least one of said body and said first discharge element when said second discharge element is coupled to said at least one of said body and said first discharge element.

35. The apparatus of claim 26 further comprising a connector operably configured to connect said body to a fluid source such that said opening receives the fluid from said fluid source.

36. The apparatus of claim 26 wherein said second discharge element defines a plurality of outlets comprising said second outlet.

37. The apparatus of claim 26 wherein said second outlet is the only outlet of said second discharge element.

38. The apparatus of claim 26 wherein said second discharge element comprises a fluid dispensing end unitarily formed with said second discharge element.

39. The apparatus of claim 26 wherein said second discharge element is attachable to and detachable from a fluid dispensing end.

40. The apparatus of claim 26 wherein the apparatus is a showerhead.

41. The apparatus of claim 26 wherein said second discharge element is operably configured to receive said at least some fluid received in said first conduit through said first outlet.

* * * * *